Figure 1:
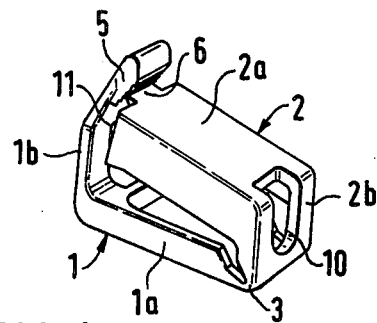

United States Patent [19]

Laszczower

[11] 4,453,295
[45] Jun. 12, 1984

[54] DEVICE FOR PINCHING-OFF HOSES

[75] Inventor: Max Laszczower, Basel, Switzerland

[73] Assignee: Solco Basel AG, Basel, Switzerland

[21] Appl. No.: 386,490

[22] Filed: Jun. 9, 1982

[30] Foreign Application Priority Data

Jun. 17, 1981 [CH] Switzerland ................... 4000/81

[51] Int. Cl.³ .............................................. F16K 7/06
[52] U.S. Cl. ....................................... 251/10; 24/543;
128/346; 24/115 G; 24/132 R; 24/487
[58] Field of Search ............. 24/248 R, 248 B, 327,
24/329, 335, 339, 132 AA, 132 WL, 115 G, 255
SL, 132 R; 128/346; D24/27; 251/10

[56] References Cited

U.S. PATENT DOCUMENTS

| 455,392 | 7/1891 | Ellis | 24/115 G |
|---|---|---|---|
| 1,580,649 | 4/1926 | Christiansen | 251/10 |
| 1,879,991 | 9/1932 | Pratt | 24/115 G |
| 3,171,184 | 3/1965 | Posse | 24/248 R |
| 3,461,876 | 8/1969 | Miller | 24/248 R |
| 3,822,052 | 7/1974 | Large | 24/255 SL |
| 3,874,042 | 4/1975 | Eddleman et al. | 128/346 |
| 3,942,228 | 3/1976 | Backman et al. | 251/10 |
| 4,235,412 | 11/1980 | Rath et al. | 24/132 R |
| 4,270,491 | 6/1981 | Cox | 24/115 G |

OTHER PUBLICATIONS

"Dura-Clamp Flow Valves for Flexible Tubing", Thermoplastic Scientifics, Inc., 1979.

*Primary Examiner*—Gene Mancene
*Assistant Examiner*—John G. Weiss
*Attorney, Agent, or Firm*—Ladas & Parry

[57] ABSTRACT

A hose clamp, which may be completely made of plastic, comprises two clamping stirrups which can be anchored in clamping position by interaction of a tongue on one stirrup and a toothed section of the other stirrup. The hose to be clamped can either extend through coaxial openings of the clamping stirrups or be introduced between the stirrups from the side. In the first case, the clamp can only be removed over a free end of the hose while, in the second case, the clamp can be positioned at any point along the hose as desired.

4 Claims, 3 Drawing Figures

DEVICE FOR PINCHING-OFF HOSES

The present invention relates to a device for pinching-off flexible hoses carrying liquid, for the purpose of cutting-off and/or regulating the through-flow, this device possessing two interacting clamping stirrups, between which the hose is nipped, the two clamping stirrups being pivotably connected to each other via an articulation-point, and securing elements being located, at the free ends of the two clamping stirrups, for anchoring the clamping stirrups in the pinching-off position.

Hoses carrying liquid, of the type, for example, used for drawing off and re-infusing blood during operations, are pinched-off by means of special devices, which allow the through-flow to be partially throttled, or even to be cut off completely.

When this is done, at least one end of the hose is, in many cases, freely accessible, while there are other applications in which both the ends of the hose are connected to equipment, or to vessels, and remain connected in this way even for a comparatively long time.

In the latter case, in which no open end of the hose is available, a clamping device can be fitted only from the direction of the periphery of the hose, and this clamping device can also be detached again at any time. If, however, the clamp remains on the hose over a comparatively long time, it would thus be desirable, precisely in this case, to have a clamp which is securely anchored to the hose, which can, in particular, be adjusted as desired, and which can even be shifted in the direction of the hose axis, but which cannot, per se, be removed without detaching an end of the hose. Nevertheless, it should still be possible, for other applications, to fit this clamp to the hose, from the outside, in such a manner that it can be removed at any time, without the necessity of detaching one of the ends of the hose in order to accomplish this.

This flexibility of application, which is demanded by practical considerations, is exhibited by none of the known hose clamps. The object of the present invention is accordingly to propose a device for pinching-off flexible hoses, this device being capable both of being fitted to the hose in a securely anchored manner, and of being easily removed, it being possible to decide, from case to case, which of the two above-mentioned methods of fitting should more advantageously be employed.

This object is achieved, according to the invention, by means of the combination of features defined in the independent patent claim 1.

Figure 2:
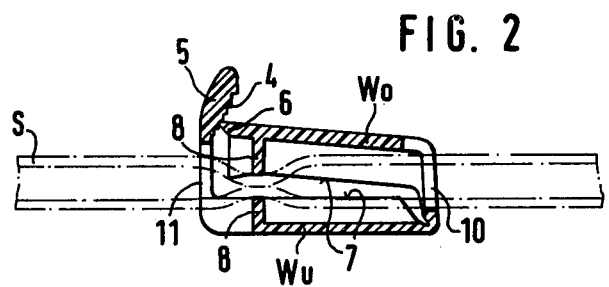
Figure 3:
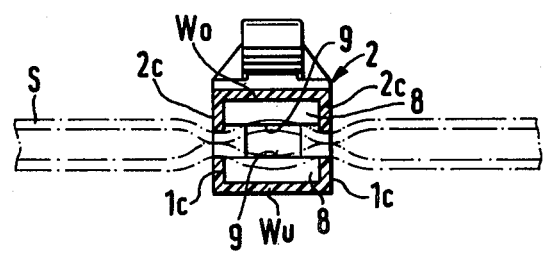

In the text which follows, an illustrative embodiment of the subject of the invention is described, by reference to the attached drawing, in which FIG. 1 shows a perspective illustration of a preferred embodiment of a device for pinching-off a flexible hose carrying liquid, FIG. 2 shows the first method of fitting, and FIG. 3 shows the second method of fitting the device to a hose which is to be pinched-off.

According to FIG. 1, the clamp possesses two clamping stirrups 1 and 2, which are connected to each other by an articulated joint 3. In a preferred embodiment, the two clamping stirrups, 1 and 2, are manufactured from plastic, in one piece, the articulated joint 3 being designed as a point of weakness, that is to say, as a point at which the wall cross-section is weaker.

The two clamping stirrups, 1 and 2, are of similar, but not identical design, and both possess, seen in their longitudinal direction, a cross-section which is virtually L-shaped. According to this, the clamping stirrup 1 comprises a long limb 1a and a short limb 1b, while the clamping stirrup 2 comprises a long limb 2a and a short limb 2b. A toothed lip 5, which is provided with teeth 4 (FIG. 2), adjoins the short limb 1b of the clamping stirrup 1, this toothed lip 5 being slightly inclined with respect to the vertical. In contrast, a sharply converging tongue 6 is molded onto the free end of the long limb 2a, this tongue engaging, in the pinching-off position, into the toothing of the toothed lip 5.

As the drawing further shows, the two clamping stirrups are designed virtually as open box-sections, that is to say, two side-cheeks 2c project downwards, in each case, from an upper wall Wo, which is horizontal in FIG. 3, while two side-cheeks 1c project upwards from the lower wall Wu. The free edges 7 of these two pairs of side-cheeks serve as clamping edges, as will be further appreciated from the functional description which follows.

As FIG. 2 further shows, a web 8 is molded onto each clamping stirrup, projecting downwards or upwards as the case may be. The two webs 8 are located in that portion of the clamp which adjoins the toothed lip 5, and their free edges 9 likewise have the function of clamping edges.

In addition, openings, 10 and 11, are respectively provided in each of the two smaller limbs, 1b and 2b, each of these openings further extending, to some extent, over the adjoining longer limb (1a or 2a), while their open cross-sections are intended to correspond to at least the full cross-section of the hose which is to be pinched-off.

According to FIG. 2, the clamp, which is described, can be used, in accordance with the first method of fitting, whereby the hose is pushed through the two openings, 10 and 11, and the clamp is operated by thumb pressure on the upper wall Wo, that is to say, the clamp is locked. At the same time, the clamping edges of the two webs 8 press against the hose.

The clamp is then held, in a convenient manner, between the thumb and the index finger, and the desired through-flow cross-section can be regulated by appropriate finger-pressure, the tongue 6 then latching into one of the tooth-gaps provided in the toothed lip 5. In the case of this method of fitting, the clamp is securely anchored to the hose, and cannot any longer detach itself, even after the pinching-off pressure is released, especially as the openings 10, 11 offer a certain frictional resistance to the hose. Although the clamp can consequently be shifted, as desired, in the direction of the hose axis, it cannot fall off, for example during operations, even if it is intended that the lower end of the hose should hang down freely.

The second method of fitting is shown in FIG. 3. Here, the open clamp is pushed over the hose, from the direction of the periphery of the hose, and is then once again actuated, between the thumb and index finger, the clamping edges of the side-cheeks 1c/2c in this case squeezing-off the hose in accordance with whatever pressure is chosen. The clamp can be removed from this position whenever desired, without any necessity to detach one of the ends of the hose, which may possibly be connected to other equipment.

Practical experience, especially the manual actions involved in the drawing-off and re-infusion of blood, which have to be carried out during operations, and which are, to some extent, tricky to perform, shows that both the methods of fitting are needed in alternation, and that the combination of these two systems in a single clamp effects not only a reduction in the procurement costs, but also provides more safety for the patient.

The hose clamp which is described is extremely simple to operate, and, in every case, leaves one of the operator's hands free for other actions. Once attached, the clamp can be released, in a convenient manner, by firmly holding the free front edge of the short limb 1b by means of the tip of the index finger, and then pressing up the toothed lip 5 by means of the thumb, which is resting on the wall Wo.

The wear-resistant plastics which are required for manufacturing a one-piece hose clamp of this type, are known to a person skilled in the art. The injection-molded part possesses all the elements which are required for the functioning of the clamp, so that no assembly of any kind, or any other processing, is required after the injection-molding operation.

In the pinched-off position, according to FIG. 2 or FIG. 3, the tongue 6 is pressed against the toothing 4 by a resilient restoring source, which opposes the pressing force of the thumb during the closing operation. This resilient restoring source is exerted by the hose S, so that the fitting of an appropriate spring element is dispensed with.

I claim:

1. A clamping device for regulating the flow of liquid passing through a flexible hose, comprising two clamping stirrups gripping the hose therebetween, the clamping stirrups being bendably connected with each other at one end thereof and carrying interacting securing elements at the opposite end thereof, said securing elements being releasable and being adapted to anchor the clamping stirrups in different positions, and further comprising in said both ends of the clamping stirrups aligned passages for receiving the hose, said clamping stirrups having a pair of interacting clamping edges arranged at right angles to a hose extending through said passages for changing the cross-section of the hose, and also two additional spaced pairs of clamping ribs extending in the direction of said passages, said clamping ribs being adapted to change the cross section of the hose when the hose extends across said clamping device at a right angle to the direction of said passages.

2. The device as claimed in claim 1, wherein the clamping stirrups are in the form of box-sections and the clamping ribs form the side walls of said box sections.

3. The device as claimed in claim 1, wherein the clamping stirrups are L-shaped, one of said securing elements having a toothed section and the other of said elements having a tongue to engage with said toothed section.

4. The device as claimed in claim 1, wherein the clamping stirrups are formed in one piece from plastic material and are bendably connected at a point of weakness in the plastic material.

* * * * *